United States Patent
Kita et al.

(10) Patent No.: US 7,096,715 B2
(45) Date of Patent: Aug. 29, 2006

(54) ODOR DISCRIMINATING APPARATUS

(75) Inventors: Jun-ichi Kita, Kyoto-fu (JP); Hirokazu Taniguchi, Osaka-fu (JP); Hisamitsu Akamaru, Osaka-fu (JP)

(73) Assignee: Shimadzu Corporation, Kyoto (JP)

( * ) Notice: Subject to any disclaimer, the term of this patent is extended or adjusted under 35 U.S.C. 154(b) by 91 days.

(21) Appl. No.: 10/924,958

(22) Filed: Aug. 25, 2004

(65) Prior Publication Data
US 2005/0044928 A1 Mar. 3, 2005

(30) Foreign Application Priority Data
Aug. 29, 2003 (JP) ............................. 2003-209583

(51) Int. Cl.
*G01N 33/497* (2006.01)
(52) U.S. Cl. ...................... 73/23.34; 73/23.2
(58) Field of Classification Search ............... 73/23.34, 73/23.2
See application file for complete search history.

(56) References Cited

U.S. PATENT DOCUMENTS 6,439,026 B1 * 8/2002 Nakano et al. ............ 73/23.34
6,494,077 B1 * 12/2002 Aoyama et al. ........... 73/23.34
6,834,530 B1 * 12/2004 Kita et al. ................. 73/23.34

FOREIGN PATENT DOCUMENTS

JP 11-352088 12/1999
JP 2002-22692 1/2002

OTHER PUBLICATIONS

Jun-ichi Kita et al., "Development of an Odor Discrimination System" Shimadzu Review, vol. 59, No. 1-2 (Nov. 2002) Shimadzu Corp., pp. 77-85.

* cited by examiner

*Primary Examiner*—Hezron Williams
*Assistant Examiner*—Rodney Frank
(74) *Attorney, Agent, or Firm*—Westerman, Hattori, Daniels & Adrian, LLP.

(57) ABSTRACT

The present invention provides an odor discriminating apparatus capable of determining the similarities or differences between plural odors with respect to the odor quality and the odor intensity, and showing the measurement result in such a manner that helps the user to correctly understand the result. According to the present invention, plural samples of a reference odor gas, each sample having a different concentration, are measured with m pieces of odor sensors. Based on the measurement result, a calibration curve is created in an m-dimensional space formed by the detection signals of the m pieces of odor sensors (Steps S1–S3). Next, a measurement point U0 representing the measurement result of a subject odor is plotted in the m-dimensional space. Based on the spatial relation between the measurement point U0 and the calibration curve, an index $\theta$ indicating the difference in the quality between the two odors and another index In indicating the difference in the intensity between the two odors are calculated (Steps S4–S9). Then, using a predetermined conversion rule, $\theta$ and In are converted into an odor quality difference index and an odor intensity difference index, and the measurement result is plotted on an odor similarity evaluation graph whose abscissa and ordinate correspond to the two indices, respectively (Step S10).

12 Claims, 3 Drawing Sheets

ODOR DISCRIMINATING APPARATUS

The present invention relates to an odor discriminating apparatus for determining the similarities or differences between odors including any kinds of scents or smells. In particular, the present invention relates to an odor discriminating apparatus suitable for examining and/or evaluating odors of food, drinks, cosmetics, medicines or other products having special odors.

BACKGROUND OF THE INVENTION

Most of the conventional methods for the instrumental analysis of odors use the component analysis with gas chromatographs or gas chromatograph mass spectrometers. The component analysis, however, is affected by various problems. For example, the measurement takes a long time and requires considerable skill. Furthermore, a large number of measurement signals is obtained for each sample, so that the analysis and interpretation of the signals are difficult and take a long time. Also, the measurement result has no correlation with the organoleptic evaluation by the olfactory sense of a human being.

To solve such problems, some odor measuring apparatuses use odor sensors responsive to odorous substances. Examples of such apparatuses are disclosed in the Japanese Unexamined Patent Publication Nos. H11-352088 and 2002-22692, and "Development of Odor Discriminating Apparatus," KITA, Junichi et al., *Shimadzu Review*, Vol. 59, No. 1–2 (November 2002), Shimadzu Corp., pp. 77–85. These apparatuses are capable of processing the detection signals produced by plural odor sensors and determining the distances between the odors of plural samples (i.e. whether or not these odors belong to the same or similar categories) by the cluster analysis, principal component analysis or other type of multivariate analysis, or by the non-linear analysis using neural networks.

For example, in the principal component analysis, a graph representing a space formed by plural axes corresponding to different principal components is created, and the results of the measurements of a large number of samples are plotted in the space as measurement points. The spatial relation between the measurement points enables the determination of the similarity or difference between the odors. However, in principle, the principal component analysis allows only a relative comparison of the sensor outputs. In this analysis, the selection of the samples to be simultaneously measured may influence the measurement result. For example, two relatively similar odors might be located very far from each other on the graph, or inversely, two odors having little similarity might be located close to each other on the graph. In such cases, the user often misunderstands the measurement result. Therefore, it is necessary to considerably limit the kinds of odors to be simultaneously measured.

According to another analysis method, the Euclidean distance between the measurement result of a reference odor and that of a subject odor is calculated, and the similarity or difference between the two odors is determined from the Euclidean distance. This method provides the absolute difference between the two odors, but it is impossible to determine whether the difference results from the quantitative difference or the qualitative difference between the odors. For example, in the evaluation of the odors of food, drinks, cosmetics, medicines or other products, it is impossible to determine whether the difference is due to a mixture of an unexpected odor in the subject odor or an excessive addition of the perfumes concerned. Therefore, the evaluation or examination result cannot always be satisfactory.

In view of the above-described problems, the present invention intends to provide an odor discriminating apparatus capable of determining the similarities or differences between plural odors with respect to the odor quality and the odor intensity. The present invention also intends to provide an odor discriminating apparatus capable of visually representing the measurement result in such a manner that helps the user to correctly understand the result and prevents the user from making a wrong determination.

SUMMARY OF THE INVENTION

To solve the aforementioned problems, the odor discriminating apparatus according to the present invention includes:

m pieces of odor sensors having different responsive characteristics, where m is an integer greater than one;

a first index calculator for calculating a first index corresponding to the difference in the quality between a reference odor and a subject odor, based on the results of the measurements of the reference odor and the subject odor carried out with the m pieces of the odor sensors;

a second index calculator for calculating a second index corresponding to the difference in the intensity between the reference odor and the subject odor; based on the results of the aforementioned measurements; and an odor difference demonstrator for demonstrating the degree of difference between the reference odor and the subject odor with respect to the odor quality and the odor intensity, using the first and second indices or other indices converted from the first and second indices.

In a mode of the present invention, the first and second index calculators are constructed to calculate the first and second indices as follows. When a certain kind of odor is measured with the m pieces of odor sensors, each odor sensor generates a different detection signal, so that m pieces of data are obtained from the signals. These data can be mathematically represented by a point in an m-dimensional space. When, for example, plural samples of the same reference odor differing from each other only in concentration are measured one after another, the aforementioned point moves in the m-dimensional space in a certain direction as the concentration changes. The movement of the point can be represented by a line (a straight line or a curve) or a vector. This line or curve is hereby defined as the calibration curve. Likewise, the measurement result of the subject odor can be represented by a measurement point in the m-dimensional space. Then, based on the relation between the measurement point and the calibration curve, the first and second indices are calculated.

The first index calculator may calculate the first index by a process including the following steps: creating an orthogonal projection of the measurement point onto the calibration curve, or a projection equivalent thereto, to locate a projective point on the calibration curve; and calculating the first index from the degree of distance between the projective point and the measurement point, or from the value obtained by normalizing the degree of distance by the distance between the projective point or measurement point and the origin (or zero point). The second index calculator, on the other hand, may calculate the second index from the degree of distance between the projective point and the origin and the degree of distance between a predetermined reference point on the calibration curve and the origin.

In another mode of the present invention, a reference point representing the measurement result of the reference odor and a measurement point representing the measurement result of the subject odor are plotted in an m-dimensional space, and a reference odor vector directed from the origin to the reference point and a subject odor vector directed from the origin to the measurement point are determined. Then, the first index calculator calculates the first index from the angle between the reference odor vector and the subject odor vector, and the second index calculator calculates the second index from the lengths of the reference odor vector and the subject odor vector.

The odor discriminating apparatus according to the present invention is capable of demonstrating the similarities or differences between the subject odor and the reference odor in the form of absolute values indicating the odor quality and the odor intensity. This improves the objectivity and accuracy of the evaluation and/or examination of odor qualities.

The odor difference demonstrator may output the measurement result in various forms on a screen or printing media. For example, it may create a graph having a first axis corresponding to the first index, or a value converted from the first index, and a second axis corresponding to the second index, or a value converted from the second index.

The above-described odor difference demonstrator definitely shows the degree of similarity or difference between the reference odor and the subject odor with respect to the odor quality and the odor intensity. This helps the user to correctly understand the result, so that even a user having little experience in the measurement can have a clear comprehension or determination of the findings.

DETAILED DESCRIPTION OF A PREFERRED EMBODIMENT

Figure 1:
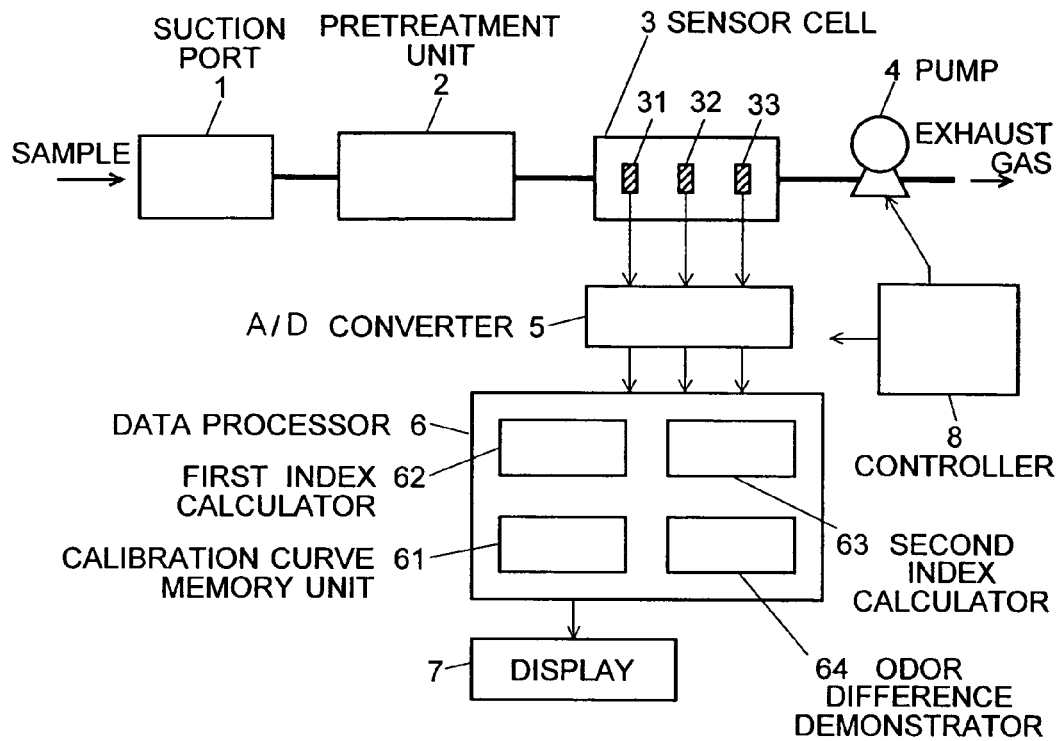
FIG. 1 is a block diagram showing the construction of the odor discriminating apparatus of the first embodiment of the present invention.

The first embodiment of the odor discriminating apparatus according to the present invention is described with reference to FIGS. 1–4. FIG. 1 is a block diagram showing the construction of the odor discriminating apparatus of the present embodiment.

The present odor discriminating apparatus includes the following elements: a suction port 1 for sucking a gas sample; a pretreatment unit 2 for performing a pretreatment of the sucked gas sample; a sensor cell 3 with plural (three in the case of FIG. 1) odor sensors 31–33 for measuring a gas sample containing various odor components, each sensor having a different responsive characteristic; a pump 4 for drawing the gas sample into the sensor cell 3; an analogue-to-digital (A/D) converter 5 for converting the detection signals of the odor sensors 31–33 into digital signals; a data processor 6 for analyzing the digitized detection data; a display 7 for displaying the analysis results on a screen; and a controller 8 for controlling the overall operation of the apparatus.

The pretreatment unit 2 performs the removal of moisture content from the sample, the condensation or dilution of the component of interest contained in the sample, the removal of the interfering components, and so on. The odor sensors 31–33 are, for example, sensors using metal oxide semiconductors whose resistances vary depending on the kind and concentration of odor components. Other examples of the odor sensors include: a sensor using conducting polymers; and a sensor using quartz resonators or SAW (surface acoustic wave) devices coated with a gas absorption film. The data processor 6 and the controller 8 are constructed using mainly a personal computer. Running a predetermined program on the personal computer enables the computer to have various functions, which will be described later.

Figure 3:
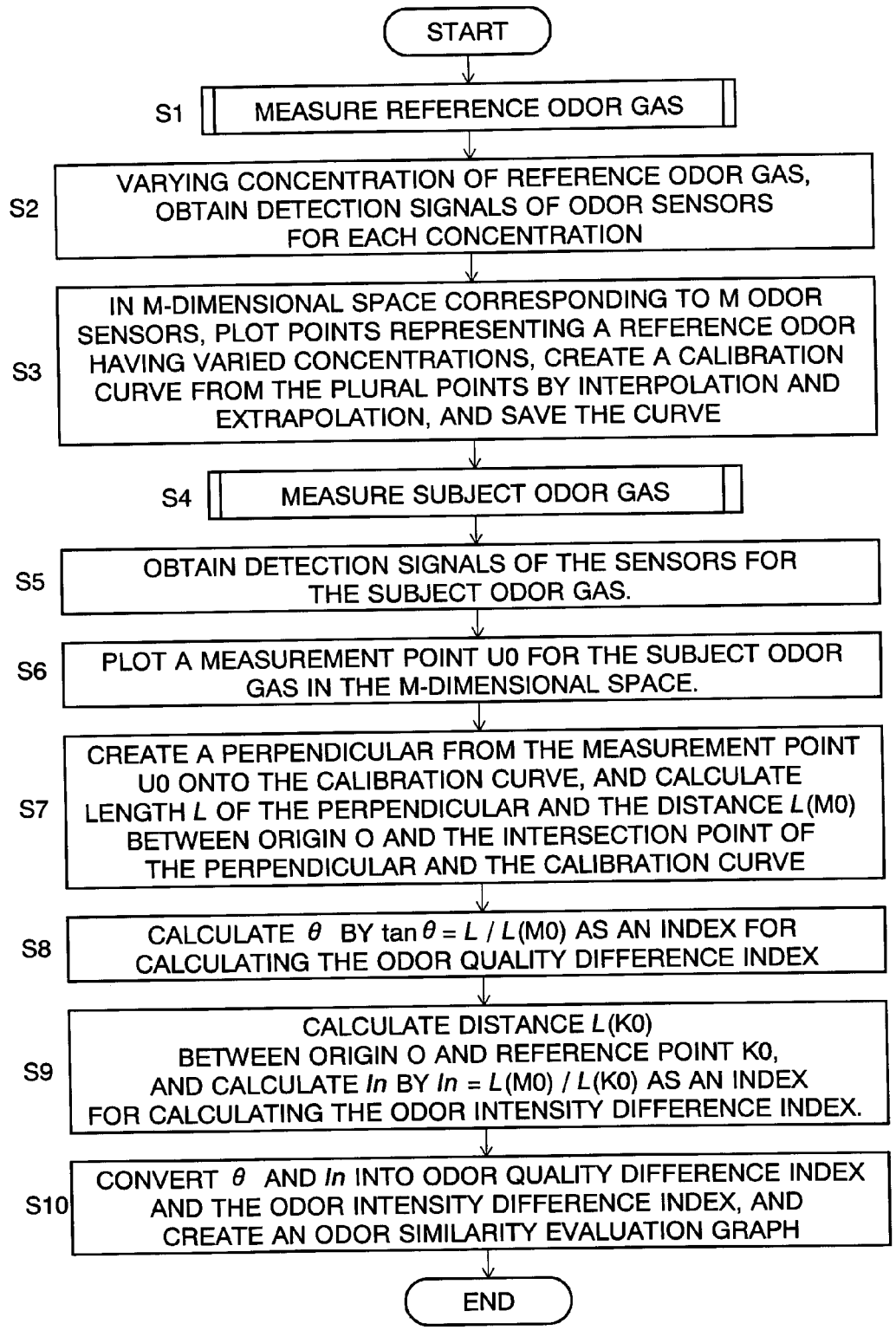
FIG. 3 is a flow chart showing the measurement steps performed by the apparatus of the first embodiment.

The odor-discriminating operation performed by the present odor discriminating apparatus controlled by the controller 8 is described, referring to the flow chart shown in FIG. 3.

In the first step, a reference odor gas to be used as the reference for evaluating a subject odor is measured (Step S1). For example, a bag containing the reference odor gas is connected to the suction port 1, and the pump 4 is energized to draw the reference odor gas through the pretreatment unit 2 into the sensor cell 3. When the components of the reference odor gas introduced into the sensor cell 3 come in contact with the odor sensors 31–33, the odor sensors 31–33 generate different detection signals in parallel. The detection signals are sampled and digitized by the A/D converter 5, which sends three pieces of detection data DS1, DS2 and DS3 to the data processor 6.

Figure 2:
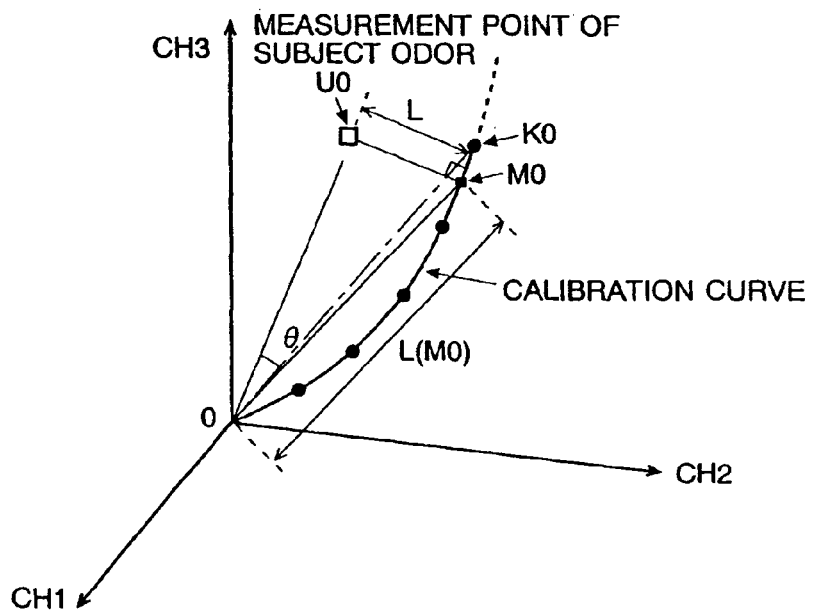
FIG. 2 is a drawing explaining the odor discriminating operation performed by the apparatus of the first embodiment.

FIG. 2 shows a three-dimensional space formed by three axes CH1, CH2 and CH3 corresponding to the three different detection signals generated by the three odor sensors 31–33. This space is called the "odor space" hereinafter. In this space, the aforementioned three pieces of detection data (DS1, DS2, DS3) are represented by a point.

The pretreatment unit 2 condenses or dilutes the reference odor gas to produce plural samples of the reference odor gas having different concentrations, and the odor sensors 31–33 generate detection signals for each sample of the reference odor gas (Step S2). This step gives plural sets of detection data (DS1, DS2, DS3) corresponding to the different concentrations of the reference odor gas. Plotting these sets of detection data in the odor space gives a series of points (DS1, DS2, DS3) aligned in a direction specific to the kind of the odor. In the three-dimensional odor space, a curve (or straight line) can be created by the interpolation or extrapolation of the aforementioned points. This curve is hereby defined as the calibration curve. The data processor 6 receives plural pieces of detection data one after another and creates the calibration curve. The data used for representing the calibration curve are stored in the calibration curve memory unit 61 (Step S3).

In most cases, the calibration curve becomes a curve instead of a straight line. Therefore, one recommendable method for creating the calibration curve from the detection data is to make an approximation using a regression curve of the 2nd, 3rd or higher order. Another method is to prepare an appropriate model formula, substitute the measurement points into that formula to determine the coefficients used in the formula, and complete an approximate formula by using the coefficients. Of course, it is possible to use other methods.

The next step is to measure the subject odor gas, i.e. the objective of the evaluation (Step S4). For example, a bag containing the subject odor gas is connected to the suction port 1, and the pump 4 is energized to draw the subject odor gas through the pretreatment unit 2 into the sensor cell 3. When the components of the subject odor gas introduced into the sensor cell 3 come in contact with the odor sensors 31–33, the odor sensors 31–33 generate different detection signals in parallel (Step S5). Then, three pieces of detection data DS1, DS2 and DS3 are sent to the data processor 6, which are represented by a point in the three-dimensional odor space. FIG. 2 shows this point as the measurement point U0 (Step S6).

The data processor 6 uses the spatial relation between the measurement point U0 and the calibration curve to determine the similarities or differences between the two odors as follows. The first step is to draw a perpendicular line from the measurement point onto the calibration curve, as shown in FIG. 2, where M0 denotes the intersection point of the perpendicular line and the calibration curve. In the case the calibration curve is indeed a curve, the intersection point M0 is chosen so that the perpendicular line is at a right angle to the tangent to the calibration curve at the point M0. In the next step, the length of the perpendicular line, i.e. the distance L between the measurement point U0 and the intersection point M0 is calculated, and also the distance L(M0) between the intersection point M0 and the origin O is calculated (Step S7). Then, an index $\theta$ is calculated in the first index calculator 62 by the following equation (Step S8):

$$\tan \theta = L/L(M0).$$

The index $\theta$ is used for calculating an odor quality difference index, which indicates the difference in the quality between the two odors.

Next, a reference point K0 is defined on the calibration point as the reference position, and the distance L(K0) between the reference point K0 and the origin O is calculated. Then, an index In is calculated in the second index calculator 63 by the following equation (Step S9):

$$In = L(M0)/L(K0).$$

The index In is used for calculating an odor intensity difference index, which indicates the difference in the intensity between the two odors. It should be noted that the reference point K0 can be arbitrarily chosen.

Figure 4:
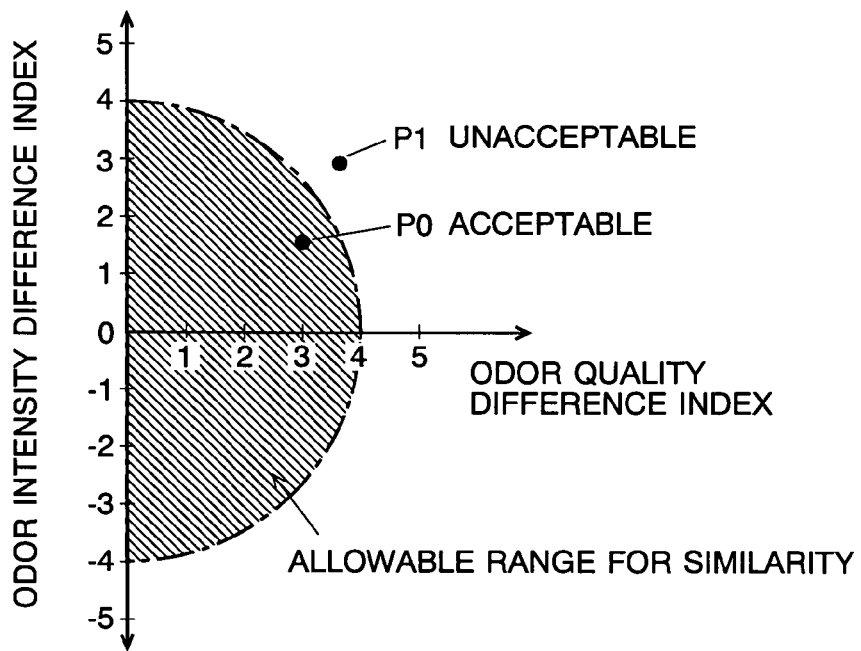
FIG. 4 is an example of the odor similarity evaluation graph created by the apparatus of the first embodiment.

Then, according to the conversion rule defined beforehand, $\theta$ and In are converted to the odor quality difference index and the odor intensity difference index. An example of the conversion rule is as follows:

(1) For every 10% increase in index In from the reference odor, the odor intensity difference index should be incremented by 1, meaning the deterioration of the similarity in the odor intensity; and (2) For every 2° increase in index $\theta$ from the reference odor, the odor quality difference index should be incremented by 1, meaning the deterioration of the similarity in the odor quality. Then, an odor similarity evaluation graph is created in the odor difference demonstrator 64 as shown in FIG. 4, where the abscissa indicates the odor quality difference index and the ordinate indicates the odor intensity difference index. This graph is displayed on the screen of the display 7 (Step S10).

For example, when $\theta = 7.43°$ and $In = 1.3$ and the above conversion rule is applied, then the odor quality difference index is approximately 3.7 and the odor intensity difference index is 3. The two indices can be represented by a point on the odor similarity evaluation graph, as indicated by point P1 in FIG. 4. This odor similarity evaluation graph shows that an odor is more similar to the reference odor as it is closer to the origin O. Therefore, if, for example, the allowance range for similarity is defined as the inside of the semicircle having a radius 4, the point P1 is unacceptable because it is outside the allowance range, whereas the point P0 is acceptable because it is inside the allowance range. From this graph, the user can easily understand that the subject odor is unacceptable. Moreover, from the position of the point P1, the user can easily understand how the point is unacceptable with respect to the odor quality and the odor intensity.

It should be noted that the aforementioned conversion rule is a mere example and other rules may be used instead.

As described above, the odor discriminating apparatus according to the present invention is capable of visually and quantitatively demonstrating the similarities or differences between the subject odor and the reference odor with respect to the odor quality and the odor intensity. Such a visual demonstration helps the user to make a correct evaluation and/or determination.

The above-described embodiment is a mere example of the present invention and may be further modified, changed or extended within the spirit and scope of the present invention. For example, the number of odor sensors is not limited to three and any number greater than one is acceptable. In general, however, it will be practically necessary to use 6–20 pieces of odor sensors. It should be noted that an odor space should be m-dimensional when m pieces of odor sensors are used.

Figure 5:
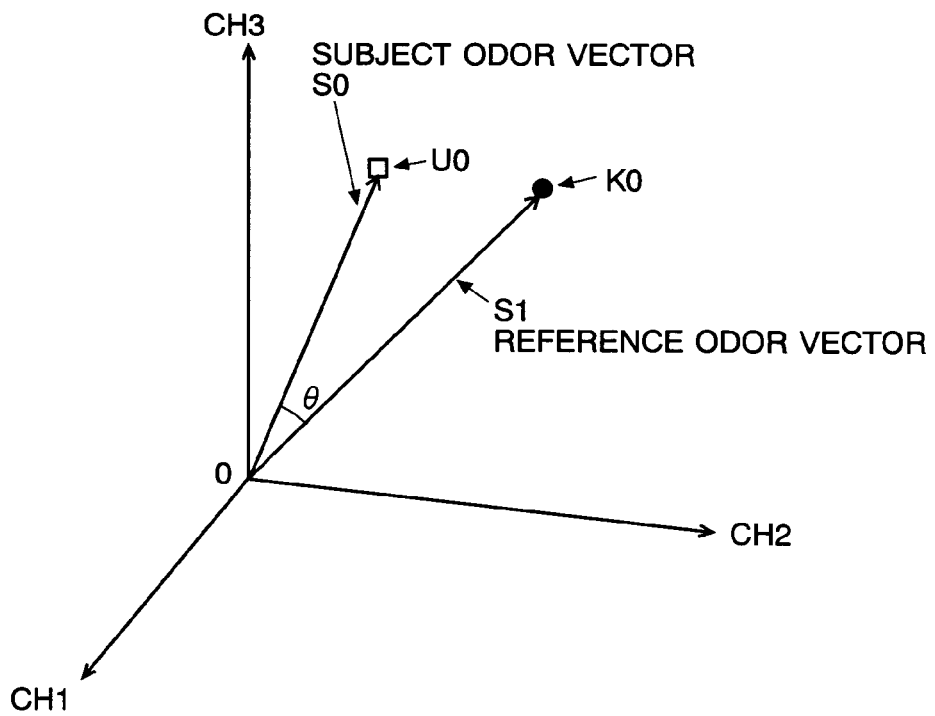
FIG. 5 is a drawing explaining the odor discriminating operation in another embodiment of the present invention.

The method of calculating the odor quality difference index and the odor intensity difference index from the measurement results of the reference odor and the subject odor is not limited to the above-described one. Referring to FIG. 5, another method of calculating the indices is described. The three-dimensional odor space in FIG. 5 (or an odor space of higher dimensions) is defined in the same manner as in the above-described embodiment.

In the three-dimensional odor space, a reference point K0 representing the detection data obtained by measuring a reference odor gas whose concentration is known and a measurement point U0 representing the detection data obtained by measuring a subject odor are plotted. Then, the subject odor vector S0 directed from the origin O to the measurement point U0 and the reference odor vector S1 directed from the origin O to the reference point K0 are created.

In the present method, the angle between the two odor vectors S0 and S1 is defined as the aforementioned index $\theta$. Also, the index In is defined by the following equation:

$$In = L(S0)/L(S1)$$

where L(S0) is the length of the subject odor vector S0, and L(S1) is the length of the reference odor vector S1. Using $\theta$ and In, the odor quality difference index and the odor intensity difference index are calculated and the odor similarity evaluation graph is created as in the above-described embodiment.

What is claimed is:

1. An odor discriminating apparatus, comprising:
   m pieces of odor sensors having different responsive characteristics, where m is an integer greater than one;
   a first index calculator for calculating a first index corresponding to a difference in quality between a reference odor and a subject odor, based on results of measurements of the reference odor and the subject odor carried out with the m pieces of the odor sensors;

a second index calculator for calculating a second index corresponding to a difference in intensity between the reference odor and the subject odor; based on the results of the aforementioned measurements; and an odor difference demonstrator for demonstrating a degree of difference between the reference odor and the subject odor with respect to odor quality and odor intensity, using the first and second indices or other indices converted from the first and second indices.

2. The odor discriminating apparatus according to claim 1, wherein:

an m-dimensional space is formed by axes corresponding to detection signals generated by the m pieces of odor sensors;

a calibration curve is created in the m-dimensional space, based on results of measurements of plural samples of the reference odors having different concentrations;

a measurement point representing the measurement result of the subject odor is plotted in the m-dimensional space;

the first index calculator calculates the first index by making an orthogonal projection of the measurement point onto the calibration curve, or a projection equivalent thereto, locating a projective point on the calibration curve, and determining the first index from a degree of distance between the projective point and the measurement point, or from a value obtained by normalizing the degree of distance by a distance between the projective point or measurement point and an origin of the m-dimensional space; and the second index calculator calculates the second index from a degree of distance between the projective point and the origin and a degree of distance between a predetermined reference point on the calibration curve and the origin.

3. The odor discriminating apparatus according to claim 1, wherein:

a reference point representing a measurement result of the reference odor and a measurement point representing a measurement result of the subject odor are plotted in an m-dimensional space formed by axes corresponding to detection signals generated by the m pieces of odor sensors;

a reference odor vector directed from an origin of the m-dimensional space to the reference point and a subject odor vector directed from the origin to the measurement point are determined;

the first index calculator calculates the first index from an angle between the reference odor vector and the subject odor vector; and the second index calculator calculates the second index from lengths of the reference odor vector and the subject odor vector.

4. The odor discriminating apparatus according to claim 1, wherein the odor difference demonstrator creates a graph having a first axis corresponding to the first index, or a value converted from the first index, and a second axis corresponding to the second index, or a value converted from the second index.

5. The odor discriminating apparatus according to claim 2, wherein the odor difference demonstrator creates a graph having a first axis corresponding to the first index, or a value converted from the first index, and a second axis corresponding to the second index, or a value converted from the second index.

6. The odor discriminating apparatus according to claim 3, wherein the odor difference demonstrator creates a graph having a first axis corresponding to the first index, or a value converted from the first index, and a second axis corresponding to the second index, or a value converted from the second index.

7. An odor discriminating method using m pieces of odor sensors having different responsive characteristics, where m is an integer greater than one, comprising steps of:

calculating a first index corresponding to a difference in quality between a reference odor and a subject odor, based on results of measurements of the reference odor and the subject odor carried out with the m pieces of the odor sensors;

calculating a second index corresponding to a difference in intensity between the reference odor and the subject odor; based on the results of the aforementioned measurements; and demonstrating a degree of difference between the reference odor and the subject odor with respect to odor quality and odor intensity, using the first and second indices or other indices converted from the first and second indices.

8. The odor discriminating method according to claim 7, wherein:

an m-dimensional space is formed by axes corresponding to detection signals generated by the m pieces of odor sensors;

a calibration curve is created in the m-dimensional space, based on results of measurements of plural samples of the reference odors having different concentrations;

a measurement point representing the measurement result of the subject odor is plotted in the m-dimensional space;

the first index is calculated by making an orthogonal projection of the measurement point onto the calibration curve, or a projection equivalent thereto, locating a projective point on the calibration curve, and determining the first index from a degree of distance between the projective point and the measurement point, or from a value obtained by normalizing the degree of distance by a distance between the projective point or measurement point and an origin of the m-dimensional space; and the second index is calculated from a degree of distance between the projective point and the origin and a degree of distance between a predetermined reference point on the calibration curve and the origin.

9. The odor discriminating method according to claim 7, wherein:

a reference point representing a measurement result of the reference odor and a measurement point representing a measurement result of the subject odor are plotted in an m-dimensional space formed by axes corresponding to detection signals generated by the m pieces of odor sensors;

a reference odor vector directed from an origin of the m-dimensional space to the reference point and a subject odor vector directed from the origin to the measurement point are determined;

the first index is calculated from an angle between the reference odor vector and the subject odor vector; and the second index is calculated from lengths of the reference odor vector and the subject odor vector.

10. The odor discriminating method according to claim 7, wherein the degree of difference is demonstrated by a graph having a first axis corresponding to the first index, or a value converted from the first index, and a second axis corresponding to the second index, or a value converted from the second index.

11. The odor discriminating method according to claim 8, wherein the degree of difference is demonstrated by a graph having a first axis corresponding to the first index, or a value converted from the first index, and a second axis corresponding to the second index, or a value converted from the second index.

12. The odor discriminating method according to claim 9, wherein the degree of difference is demonstrated by a graph having a first axis corresponding to the first index, or a value converted from the first index, and a second axis corresponding to the second index, or a value converted from the second index.

* * * * *